US00PP12556P2

(12) United States Plant Patent

Olesen et al.

(10) Patent No.: US PP12,556 P2

(45) Date of Patent: Apr. 16, 2002

(54) SHRUB ROSE PLANT NAMED 'POULTUMB'

(76) Inventors: L. Pernille Olesen; Mogens N. Olesen, both of Hillerødvejen 49, DK-3480, Fredensborg (DK)

( * ) Notice: Subject to any disclaimer, the term of this patent is extended or adjusted under 35 U.S.C. 154(b) by 0 days.

(21) Appl. No.: 09/274,685

(22) Filed: Mar. 24, 1999

(51) Int. Cl.[7] ..... A01H 5/00

(52) U.S. Cl. ..... Plt./103

(58) Field of Search ..... Plt./107, 103

(56) References Cited

PUBLICATIONS

UPOV–ROM, 2000/04, Plant Variety Database, GTI Jouve Retrieval Software, 2 citations for 'POULtumb'.*

Copy of Certificate of Grant EU3226 dated Jul. 20, 1998 and application No. EU 97/0124 dated Jan. 27, 1997.*

Copy of PL PBR 0307, dated Mar. 27, 1998 and Grant #01148 dated Feb. 24, 2000.*

* cited by examiner

*Primary Examiner*—Howard J. Locker

(57) ABSTRACT

A new garden rose plant which has abundant, white flowers and attractive, disease resistant foliage. This new and distinct variety has shown to be uniform and stable in the resulting generations from asexual propagation.

1 Drawing Sheet

SUMMARY OF THE INVENTION

The present invention constitutes a new and distinct variety of garden rose plant which originated from a controlled crossing between an unnamed seedling (non-patented) and *R. multiflora* 'Nana' (non-patented)The two parents were crossed and the resulting seeds were planted in a controlled environment. The new variety is named 'POULtumb'.

The new rose may be distinguished from its seed parent, unnamed seedling, by the following combination of characteristics:

1. The seed parent has small, deep pink colored flowers while 'POULtumb' has small white flower;
2. The seed parent is a floribunda rose with a bushy upright habit; whereas, 'POULtumb' is low growing with a more spreading habit.

The new variety may be distinguished from its pollen parent *R. multiflora* 'Nana' by the following combination of characteristics:

1. The pollen parent is miniature rose; whereas, 'POULtumb' is a low growing shrub rose;
2. The pollen parent blooms recurrently for 8–10 weeks; whereas, 'POULtumb' blooms continuously throughout the growing season.

The objective of the hybridization of this rose variety for garden use was to create a new and distinct variety with unique qualities, such as:

1. Uniform and abundant flowers;
2. Vigorous, compact growth;
3. Disease resistance;
4. Continuous blooming.

This combination of qualities is not present in previously available commercial cultivars of this type and distinguishes 'POULtumb' from all other varieties of which we are aware. As part of their rose development program, L. Pernille Olesen and Mogens N. Olesen germinated the seeds from the aforementioned hybridization and conducted evaluations on the resulting seedlings in a controlled environment in Fredensborg, Denmark. 'POULtumb', was selected by the inventors in the spring of 1987 as a single plant from the progeny of the aforementioned hybridization.

Asexual reproduction of 'POULtumb' by traditional budding was first done by L. Pernille and Mogens N. Olesen in August 1987 in a nursery in Fredensborg, Denmark. This initial and other subsequent propagations conducted in controlled environments have demonstrated that the characteristics of 'POULtumb' are true to type and are transmitted from one generation to the next.

BRIEF DESCRIPTION OF THE DRAWING

The accompanying color illustration shows a true as is reasonably possible to obtain in color photographs of this type, the typical characteristics of the buds, flowers, leaves and stems, of 'POULtumb'. Specifically illustrated in SHEET 1:

1. Stem showing branching and the attachment of leaves, buds, and peduncles;

2. Flower bud, partially opened bud, and open bloom;

3. Flower petals, detached;

4. Sepals, receptacle, and pedicel;

5. Two bare stems;

6. Leaves.

DETAILED DESCRIPTION OF THE VARIETY

The following is a description of 'POULtumb', as observed in its outdoor growth in a field nursey in Jackson County, Oreg. Observations were conducted during October, 1998. Color references are made using The Royal Horticultural Society (London, England) Colour Chart, 1995, except where common terms of color are used.

For a comparison, several physical characteristics of the rose variety 'POULfan', a shrub rose variety from the same inventors described and illustrated in U.S. Plant Pat. No. 9,641 and issued on Sep. 10, 1996 are compared to 'POULtumb' in Chart 1.

CHART 1

| | 'POULtumb' | 'POULfan' |
|---|---|---|
| Innermost petal color, upper side, upon opening. | White Group 155C with intonations of Orange-White Group 159D. | Near Red Group 49A. |
| Size of plant. | 80 cm. height by 100 cm. width. | 107–124 cm. height by 122 width. |

Parents:
*Seed parent.*—Unnamed seedling.
*Pollen parent.*—*R. multiflora* 'Nana'.
Classification:
*Botanical.*—*Rosa hybrida.*
*Commercial.*—Shrub.

FLOWER AND FLOWER BUD

Blooming habit: Continuous.
Flower bud:
*Size.*—Upon opening, 15 mm in length from base of receptacle to end of bud.
*Bud form.*—Short, pointed ovoid.
*Bud color.*—As sepals unfold, Red Group 49D. Red Group 36D at ¼ opening.
*Sepals.*—Yellow-Green Group 144A. Strong foliaceous appendages on three of the five sepals. Surfaces of sepals moderately pubescent on interior of sepals. Stipitate glands are abundant on the exterior of the sepals.
*Receptacle.*—Surface: Moderately covered with very fine stipitate hairs which are smaller then stipitate hairs present on sepals and peduncle. Shape: Pear shaped. Size: Small, 4 mm(h)×3 mm(w). Color: Green Group 144B, with some anthocyanin noted in color range Greyed-Purple Group 184B. with some anthocyanin noted in color range Greyed-Purple Group 184B.
*Peduncle.*—Surface: Large quantity of stipitate glands in color range Greyed-Purple Group 184B–184C. Length: 20 mm to 30 mm average length. Color: Greyed-Purple Group 183B is the predominant color, with intonations of Green Group 144A. Strength: Upright.
*Borne.*—Generally multiple buds per stem. with 6 to 10 buds per flowering stem.
Flower bloom:
*Fragrance.*—Light, wild rose scent that is attractive to bees and other insects.
*Duration.*—As a cut flower 1 to 2 days. The blooms have a duration on the plant of approximately 3 to 4 days. Petals fall cleanly away from plant. Individual flowers are short lived, but are replaced by other flowers opening on same stem.
*Size.*—Average open flower diameter is 30 mm.
*Form.*—Semi-double.
*Shape of flower when viewed from the side.*—Upon opening, upper part: Convex. Upon opening, lower part: Flat. Open flower, upper part: Flattened convex. Open flower, lower part: Concave.
*Petalage.*—Semi-double; Average range: 9–12 petals under normal conditions with no petaloids.
Color:
*Upon opening petals.*—Outermost petals: Upper Surface: White Group 155C with intonations of Red Group 36D. Reverse Side: White Group 155C with intonations of Orange Group 159D. Innermost petals: Upper Surface: White Group 155C with intonations of Orange-White Group 159B. Reverse Side: Yellow-White Group 158C.
*Upon opening, basal petal spots.*—Outermost petals: Outer Side: Yellow Group 4B. Inner Side: Yellow Group 10B. Innermost petals: Outer Side: Yellow Group 13A. Inner Side: Yellow Group 13B.
*After opening, petals.*—Outermost petals: Upper Surface: White Group 155B. Reverse Side: White Group 155B. Innermost petals: Upper Surface: White Group 155B. Reverse Side: White Group 155B. Basal Petal Spots: No distinctive coloration at the base of the petal noted.
General tonality: On ¾ open flower, White Group 155C with some coloration of Red Group 36D. No change in the general tonality at the end of the 1st day. After first day, general tonality is White Group 155B, with no change in tonality until petals drop.
Petals:
*Petal reflex.*—Slightly.
*Petal edge.*—With notch in center of margin.
*Shape.*—Deltoid shaped.
*Petaloids.*—None.
*Thickness.*—Thin, almost transparent.
*Arrangement.*—Informal.
Reproductive organs:
*Pollen.*—Color: Yellow-Orange Group 22A. Quantity: Average.
*Anthers.*—Size: Small. Color: Yellow Group 16D. Quantity: Average.
*Filaments.*—Color: Yellow-Orange Group 17C.
*Stigmas.*—When flower is ¾ open anthers and stigmas are the same height. Color: Yellow-Green Group 145C.
*Styles.*—Color: Yellow-Green Group 145A.
*Hips.*—None observed.

PLANT

Plant growth: Moderate, upright to bushy. Plant habit is unusual. The stems grow upward in almost a vase-like shape with flowers borne on the tops in clusters. When grown as a budded field grown plant on *Rosa multiflora* understock, the average height of the plant itself is 80 cm and the average width is 100 cm.
Stems:
*Color.*—Young wood: Yellow-Green Group 146D. Older wood: Yellow-Green Group 146C.
*Thorns.*—Incidence: 2 to 4 per 10 cm of flowering stem. Size: Average length: 5 mm. Color: Greyed-Red Group 180B at tip, with base being closer to Yellow-Green 146D. Shape: Concave, curving downward.
*Surface.*—Young wood: Smooth. Older wood: Smooth.
Plant foliage: Normal number of leaflets on leaves in middle of the stem: 5 leaflets.
*Leaf size.*—75–95 mm (l)×55–65 mm (w).
*Quantity.*—Very abundant.
*Color.*—Upper Leaf Surface: Yellow-Green Group 147A. Lower Leaf Surface: Yellow-Green Group 147B. Juvenile foliage: Upper surface is Yellow-Green Group 146B; lower surface is Yellow-Green Group 146D. Anthocyanin: None observed.
Plant leaves and leaflets:

*Stipules.*—Size: 12 mm–15 mm. Color: Top, Greyed-Purple Group 184B with Green margin Yellow-Green Group 144A. The lower portion is Yellow-Green Group 144A. Stipitate glands: Moderate number on lower side of stipule, and a limited hairs along the margins.

*Petiole.*—Length: 15 mm–18 mm. Color: Yellow-Green Group 144A. Underneath: Abundant stipules and a number of small prickles. Margins: Stipules located along the margin.

*Rachis.*—Color: Yellow-Green Group 144A. Underneath: Small prickles and a small number of stipitate glands. Margins: Stipitate glands present in moderate quantity.

*Leaflet.*—Edge: Finely serrated. Shape: Ovate. Texture: Glossy, thin.

Disease resistance: Exceptional resistance to mildew, black spot, and Botrytis under normal growing conditions in Jackson County, Oreg.

Cold hardiness: 'POULtumb' has been found to be cold hardy in Fredensborg, Denmark and in Jackson County, Oreg.

We claim:

1. A new and distinct variety of rose plant of the shrub class, substantially as herein illustrated and described as a distinct and novel rose variety due to its abundant, white flowers, vigorous growth, disease resistance, and extended period of bloom.

* * * * *

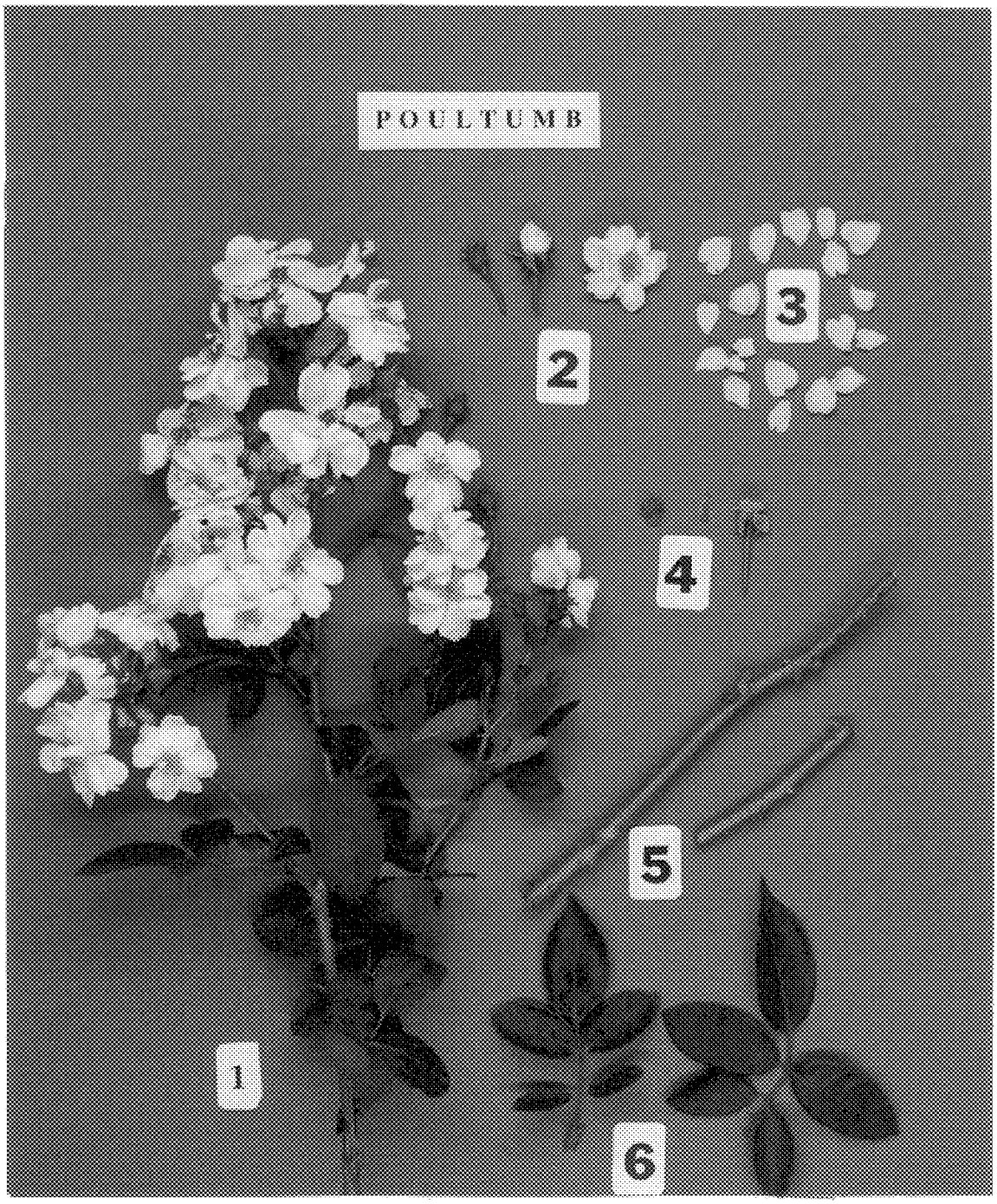
POULTUMB
1
2
3
4
5
6